United States Patent [19]

Rosenbluth et al.

[11] Patent Number: 5,007,898
[45] Date of Patent: Apr. 16, 1991

[54] BALLOON DILATATION CATHETER

[75] Inventors: Robert F. Rosenbluth, Laguna Niguel; Jay A. Lenker, Laguna Beach; George R. Greene, Costa Mesa, all of Calif.

[73] Assignee: Advanced Surgical Intervention, Inc., San Clemente, Calif.

[21] Appl. No.: 201,686

[22] Filed: Jun. 2, 1988

[51] Int. Cl.$^5$ ............................................. A61M 29/02
[52] U.S. Cl. ...................................... 604/54; 604/101; 604/264; 606/108; 606/192
[58] Field of Search ........................ 606/192, 108; 604/96–103, 264, 280; 128/898, 7, 693; 600/18

[56] References Cited

U.S. PATENT DOCUMENTS

| | | | |
|---|---|---|---|
| 2,799,273 | 7/1957 | Oddo | 604/101 |
| 2,936,760 | 5/1960 | Gants . | |
| 3,045,677 | 7/1962 | Wallace | 604/101 |
| 3,720,199 | 3/1973 | Rishton et al. | 600/18 |
| 3,835,842 | 9/1974 | Iglesias | 128/7 |
| 3,848,602 | 11/1974 | Gutnick | 606/193 |
| 3,977,408 | 8/1976 | MacKew | 606/192 |
| 4,396,021 | 8/1983 | Baumgartner | 128/7 |
| 4,461,280 | 7/1984 | Baumgartner | 128/7 |
| 4,561,446 | 12/1985 | Hetz . | |
| 4,587,975 | 5/1986 | Salo et al. | 128/693 |
| 4,636,346 | 1/1987 | Gold et al. | 604/280 |
| 4,660,560 | 4/1987 | Klein . | |
| 4,664,114 | 5/1987 | Ghodsian | 604/104 |
| 4,733,652 | 3/1988 | Kantrowitz | 600/18 |
| 4,744,366 | 5/1988 | Jang . | |
| 4,763,654 | 8/1988 | Jang . | |
| 4,819,664 | 4/1989 | Nazari | 604/96 |
| 4,838,881 | 6/1989 | Bennett | 604/280 |

FOREIGN PATENT DOCUMENTS 0351634  12/1977  France ................. 604/101

OTHER PUBLICATIONS 510 (K) Premarket Notification ASI Urethral Dilation Catheter.
W. Deising, Transurethral Dilation of the Prostate, 1956, pp. 158-171, Urol. International. 2.

Primary Examiner—Stephen C. Pellegrino
Attorney, Agent, or Firm—Knobbe, Martens, Olson & Bear

[57] ABSTRACT

Disclosed is an apparatus and method for the treatment of the symptoms of obstructive prostatism. The apparatus comprises an expandable dilatation catheter and an axially elongate sheath, adapted for transurethral insertion via the external opening of the urethra. The sheath is ellipsoid in cross-section, and provides an initial path through which the catheter and a standard cystoscope lens is guided. Disposed near the proximal end of the expandable dilation portion of the catheter is a plurality of irrigation ports. A saline solution travels through an irrigation conduit and is secreted through the irrigation ports so as to flush away blood, etc., away from the lens of a cystoscope and provides the urologist with an unobstructed view of the dilation catheter and external urethral sphincter muscle. Once the catheter has been properly positioned with respect to both the bladder neck and the sphincter, the dilation balloon may be inflated to force open the affected prostatic urethra and eliminate the obstruction.

16 Claims, 5 Drawing Sheets

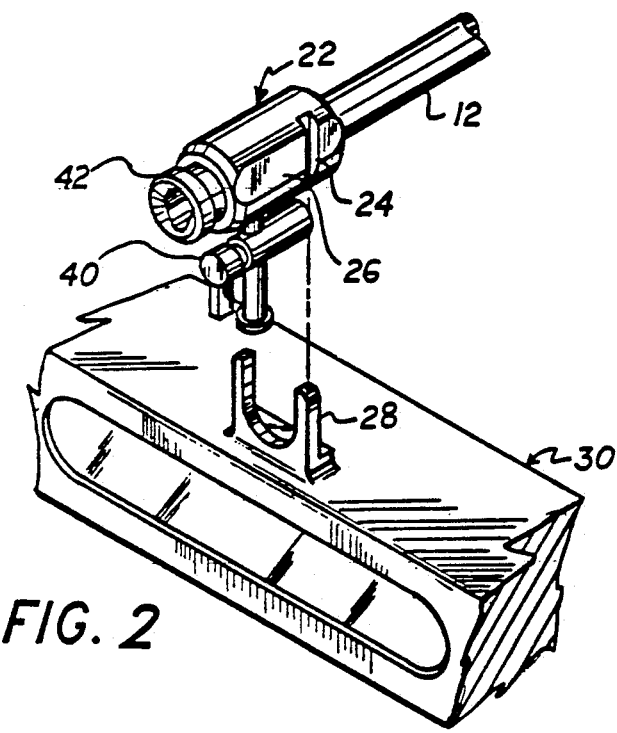
FIG. 2
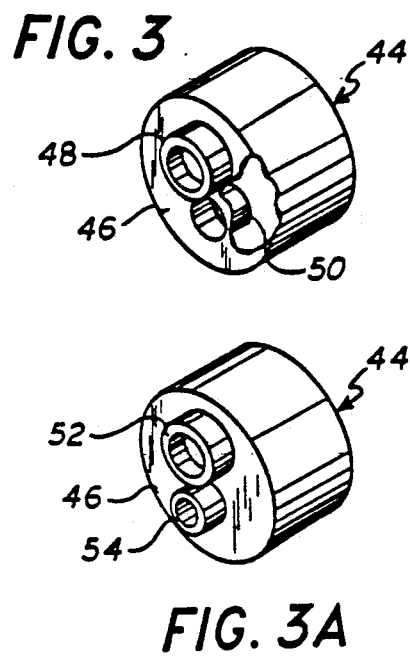
FIG. 3
FIG. 3A
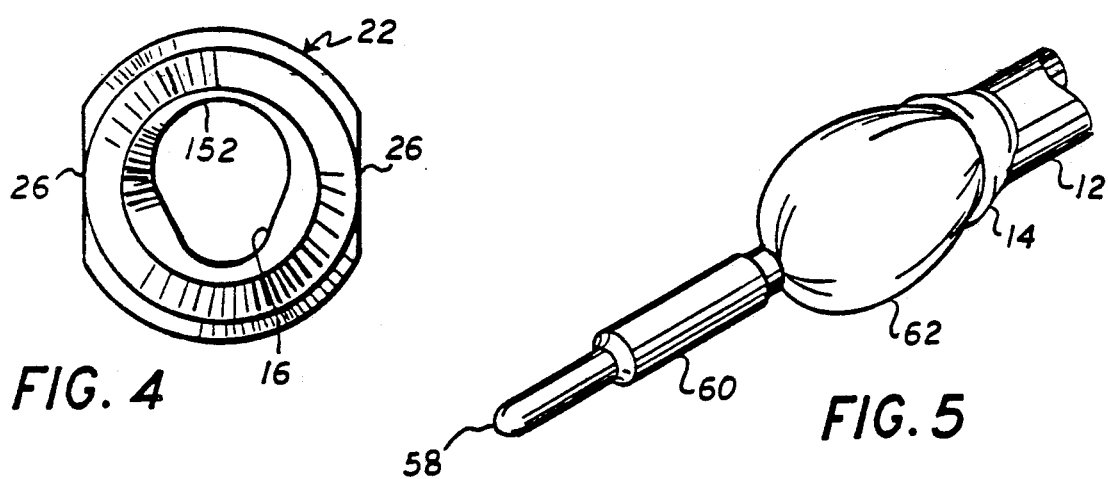
FIG. 4
FIG. 5
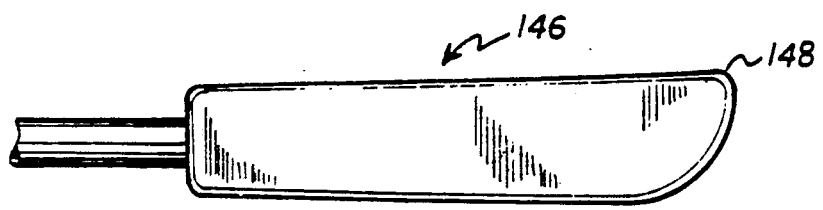
FIG. 6

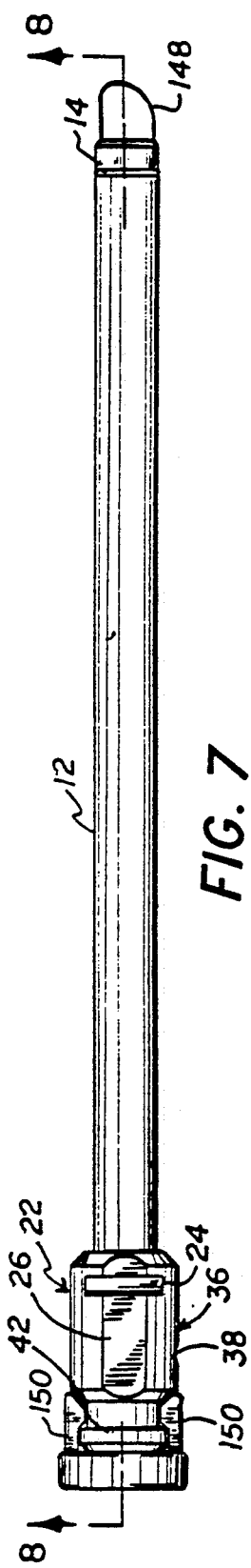
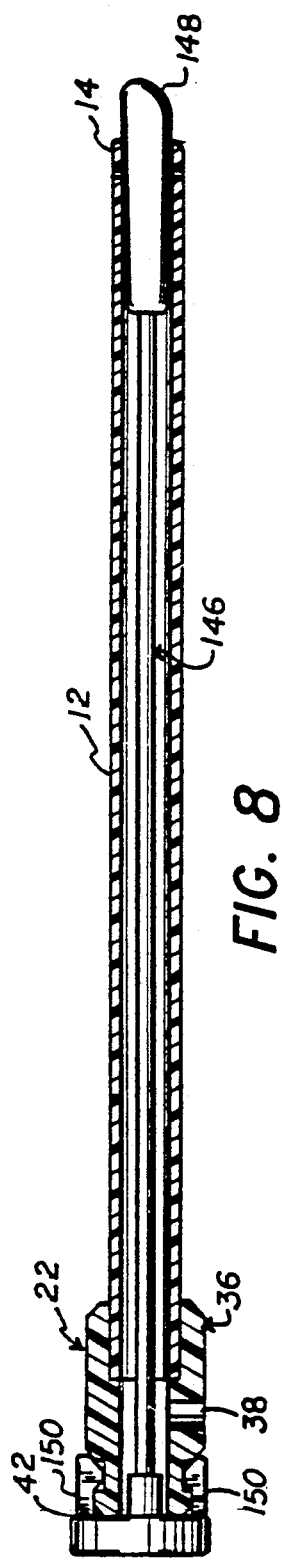
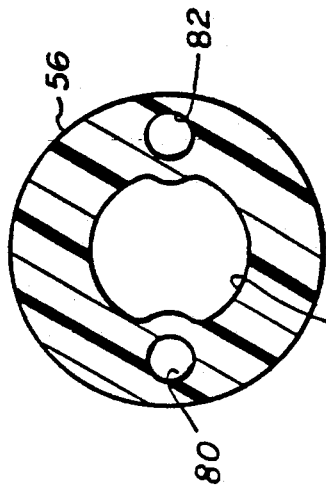
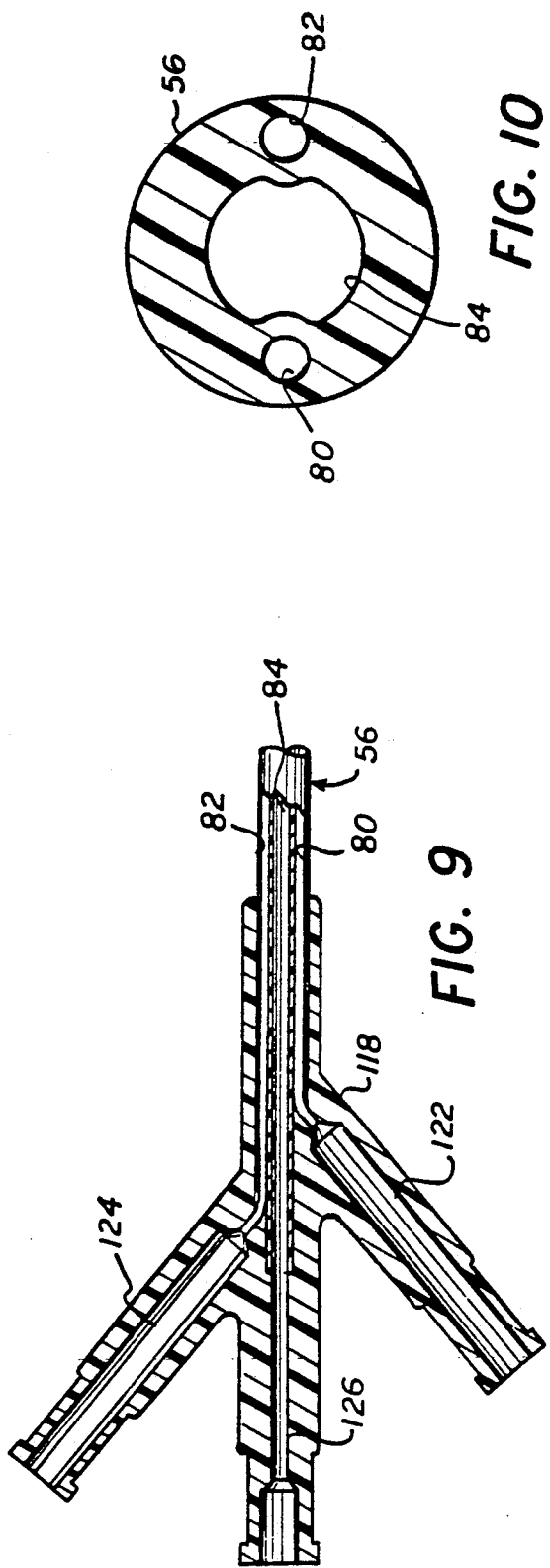

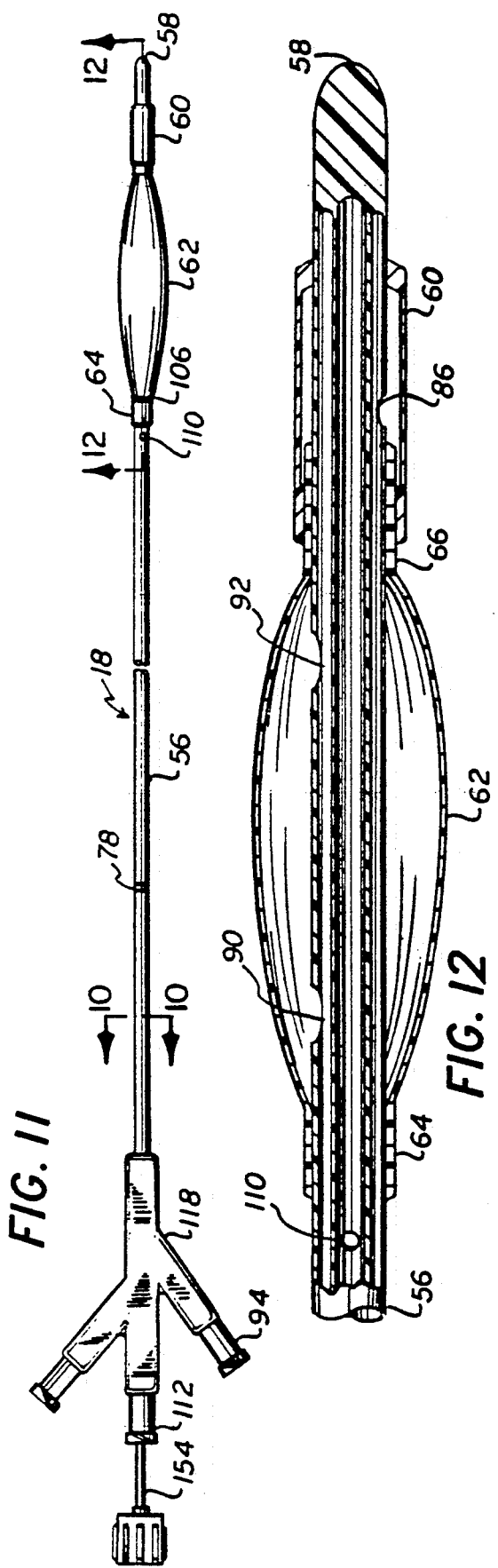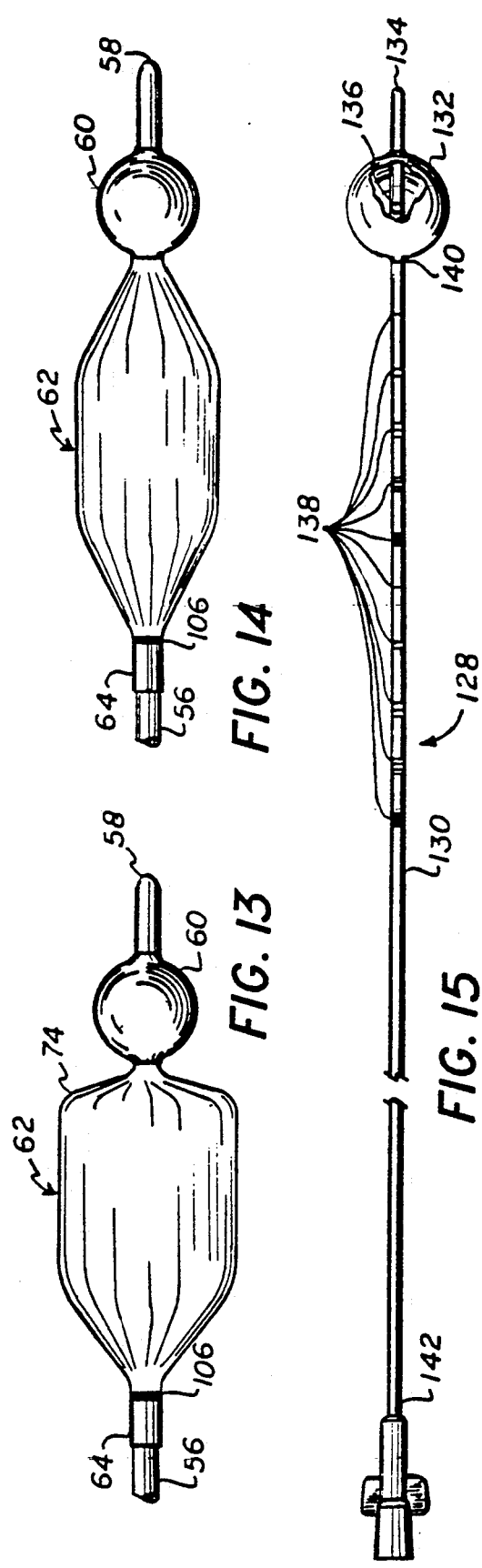

BALLOON DILATATION CATHETER

BACKGROUND OF THE INVENTION

The present invention relates generally to the field of catheters. More specifically, the present invention relates to catheters which are adapted to be inserted into the urethral lumen to alleviate obstructive prostatism, a condition quite common in males over the age of 50.

The prostate is a somewhat pear-shaped gland that extends around the urethral lumen from the neck of the bladder to the pelvic floor. Because of the close relationship of the prostate to the urethra, enlargement of the prostate, usually referred to as hypertrophy or hyperplasia, may fairly quickly obstruct the urethra, particularly if the hyperplasia occurs close to the lumen. Such an obstruction inhibits normal micturition, which causes an accumulation of urine in the bladder.

The surgical treatment of hyperplasia of the prostate gland has been a routine procedure in the operating room for many years. One method of surgical treatment is open prostatectomy whereby an incision is made to expose the enlarged prostate gland and remove the hypertrophied tissue under direct vision. Another method of treating obstructive prostatism is a technique known as transurethral resection. In this procedure, an instrument called a resectoscope is placed into the external opening of the urethra and an electrosurgical loop is used to carve away sections of the prostate gland from within the prostatic urethra under endoscopic vision.

The technique of transurethral resection offers many benefits to the patient as compared to open prostatectomy. Using this technique, the trained urologist can remove the hypertrophied prostate with less patient discomfort, a shorter hospital stay and lower rates of mortality and morbidity. Over 333,000 patients underwent this procedure in the United States in 1985, with an average hospital stay of six days. Notwithstanding the significant improvement in patient care resulting from the widespread application of transurethral resection, there remains a need for a less invasive method of treating the symptoms of prostate disease.

One of the earliest methods of relieving acute urinary retention, a symptom associated with prostate disease, was the placement of a catheter through the external urethral opening into the bladder, thereby allowing the outflow of urine from the bladder by way of the catheter lumen. These urinary catheters typically employ a balloon at the tip which, when inflated, prevents the expulsion of the catheter from the body. However, due to problems of infection, interference with sexual activity, and maintenance involved with such catheters, they are generally unacceptable for long term treatment of micturition problems.

U.S. Pat. No. 4,432,757 to Davis, Jr. teaches the use of an indwelling urethral catheter assembly, having a Foley-type balloon disposed near the distal end thereof and a substantially non-compliant balloon lead shaft proximate to the Foley-type balloon. The device is adapted to be inserted through the urethra up into the bladder. The Foley-type balloon and the balloon lead shaft are then inflated, although the balloon lead shaft remains relatively non-compliant and therefore does not expand appreciably. Gentle traction is then applied to a catheter sleeve head to sever the sleeve from the remainder of the catheter, leaving the balloon lead shaft in position within the urethra.

Another method of treating hypertrophy of the prostate gland without the need for surgery has been to inject medications into the prostate gland by means of a catheter. Such a device is disclosed in U.S. Pat. No. 550,238 to Allen, wherein two balloons are disposed along two sections of a catheter, and inflated to isolate an area within the urethra prior to the injection of the medication. However, these injections are frequently ineffective as the prostate gland exhibits only a limited ability to absorb the injected antibiotics, and proper positioning and retaining of the catheter with respect to the affected area is extremely difficult.

A substantial improvement in an apparatus and corresponding method of treatment for obstructive prostatic hypertrophy is disclosed in Klein, U.S. Pat. No. 4,660,560. In Klein's method, a calibrating catheter is used to measure the distance between the neck of the bladder and the bottom of the prostate gland. A dilatation catheter, having an annular balloon with a length equivalent to the measured length, and a Foley-type balloon at the distal end thereof is then inserted into the urethra until the Foley-type balloon is within the bladder. The Foley balloon is then inflated in the bladder and is used to position the dilatation balloon in the prostrate. The latter balloon is then inflated, to force the prostate away from the urethral lumen. Use of the Klein catheter can effectively eliminate uncertainty regarding positioning of the upper (distal) end of the dilatation balloon, thereby significantly facilitating the treatment of prostatic hypertrophy.

In practicing the Klein method, after the calibration catheter is used to measure the length of the affected prostate, it is withdrawn from the urethra, and the dilatation catheter is then inserted. Proper insertion of the dilatation catheter is crucial, as stretching of the external urethral sphincter muscle, which lies just below the prostate, could cause incontinence. Although some means of visualizing placement of the proximal end of the dilatation balloon is therefore desirable, the catheter is too large to fit through a conventional cystoscope sheath. Moreover, bleeding, which is common during such a procedure, not infrequently obscures the field of view of a cystoscope lens, making it useless.

Accordingly, in practicing the method of the Klein patent, there is a need for a method and apparatus to permit effective and sure positioning of the proximal end of the dilatation balloon with respect to the external urethral sphincter. There is a particular need to permit visualization of the balloon placement in vivo during the course of the surgical procedure.

SUMMARY OF THE INVENTION

Briefly, the present invention provides a dilatation catheter and sheath of novel design for use as a non-surgical alternative to the treatment of the symptoms of obstructive prostatism.

Advantageously, the sheath for the catheter of the present invention is uniquely sized and shaped so as to provide a path through which the catheter may travel, and leaves sufficient room for a standard cystoscopic lens. Preferably, the sheath is elliptically shaped so as to minimize the circumference thereof. The proximal end of the dilatation balloon is marked with a heavy line which may be viewed by the urologist through the lens. To facilitate the urologist's view within the urethra, or other bodily organ, an irrigation conduit is provided in the catheter. Saline or other irrigating solution is allowed to flow through the irrigation conduit, to an area proximate the line at the proximal end of the dilatation balloon. The saline solution flushes the blood associated with the procedure away from the lens, so that the urologist's view is no longer obstructed.

A significant feature of the dilatation catheter of the present invention is the unique, squared-off configuration of either or both end of the dilatation balloon. This feature enables dilatation of the affected prostatic urethra, in close proximity to the bladder and/or external urethral sphincter muscle without inadvertent dilatation of these structures. Due to the fact that common angioplasty balloons are, in general, not strong enough withstand the pressures necessary to properly dilate the prostate, the dilatation balloon of the present invention is made from a material which has a high tensile strength, rated at between 20,000 to 50,000 psi., and although somewhat stiff, is of a sufficiently small thickness so as to provide a catheter which is of substantially the same size and shape of that of the unstretched lumen.

Another significant advantage of the present invention is that the sheath is provided with a flexible tip which readily deforms to accommodate the sharp edges which may form when the dilatation balloon is deflated. The sheath also performs the function of evacuating the irrigation fluid from the urethral lumen during the irrigation process.

Yet another key feature of the present invention is the ability to yield optimal dilatation of the prostate, even at the proximal and distal edges of the affected prostatic urethra. This is accomplished by subjecting the balloon material to elevated temperatures, controlled internal pressures and axial tension during the molding process, which stretch the balloon both axially and radially to form a balloon having a somewhat squared configuration at one or both ends.

In accordance with one aspect of the present invention, there is provided an intraurethral dilatation device for relieving the symptoms of obstructive prostatism which is adapted for easy insertion into the urethra for pressure dilatation of the prostate, so as to force the prostate away from the urethral lumen and thereby eliminate the obstruction. The dilatation device includes an introduction sheath, suitable for housing a catheter and a cystoscope lens; a catheter shaft having a plurality of lumen therethrough; an expansible locating balloon, disposed near the distal tip of the catheter which, when inflated within the bladder, will provide an anchor with the bladder neck; and a dilatation balloon, proximate the locating balloon which, when inflated, conforms to a preselected configuration, so as to radially outwardly dilate the obstruction away from the urethral lumen.

In an alternative embodiment, the means for inflating the dilatation catheter is provided with a clipping mechanism which is adapted to receive a portion of the sheath, and enable the urologist to perform the procedure without assistance. Advantageously, the clip is situated on the inflation device such that the urologist may view the location of the dilatation balloon through the endoscopic lens with one eye and at the same time monitor the pressure gauge with the other eye.

Further objects, features and other advantages of the present invention will become apparent from the ensuing detailed description, considered together with the appended drawings.

BRIEF DESCRIPTION OF THE DRAWINGS

FIG. 2 is a partial assembly view of the clipping mechanism;

FIG. 3 is a perspective view of a septum, showing an inwardly extending boot sleeve in cut away;

FIG. 3a is a perspective view of a second type of septum, having both boot sleeves projecting outwardly;

FIG. 4 is an end view of the sheath, showing the unique ellipsoid shape of the inner walls thereof;

FIG. 5 is a perspective view of the tip of the sheath, as being deformed by a once-inflated dilatation balloon, so as to guide the balloon into the sheath before removal from the urethral lumen;

FIG. 6 is a side view of the tip of an obturator;

FIG. 7 is a side view of the sheath, having an obturator disposed therein, as ready for insertion into the urethra;

FIG. 8 is a cross-sectional view, taken along line 8—8 of FIG. 7, showing in more detail the obturator removably disposed therein;

FIG. 9 is a cross-sectional view, illustrating a plastic manifold disposed at the proximal end of the dilatation catheter during the molding process;

FIG. 10 is a cross-sectional view, taken along line 10—10 of FIG. 11, showing the lumen arrangement within the catheter shaft;

FIG. 11 is a side view of a dilatation catheter, having a stylet removably inserted therein;

FIG. 12 is a cross-sectional view, taken along line 12—12 of FIG. 11, showing the overlap of the shoulder of the locating balloon with the shoulder of the dilatation balloon;

FIG. 13 is a side view of a dilatation balloon, in an inflated state, exhibiting a squared-off configuration at one end, and a tapered configuration at the opposite end thereof, in accordance with one embodiment of the present invention;

FIG. 14 is a side view of a dilatation balloon, having both ends in a tapered configuration, in accordance with an alternative embodiment of the present invention;

FIG. 15 is a side view of a calibration catheter, showing a partial cut away view of an inflation aperture for the expandable balloon;

DETAILED DESCRIPTION OF THE PREFERRED EMBODIMENT

Figure 1:
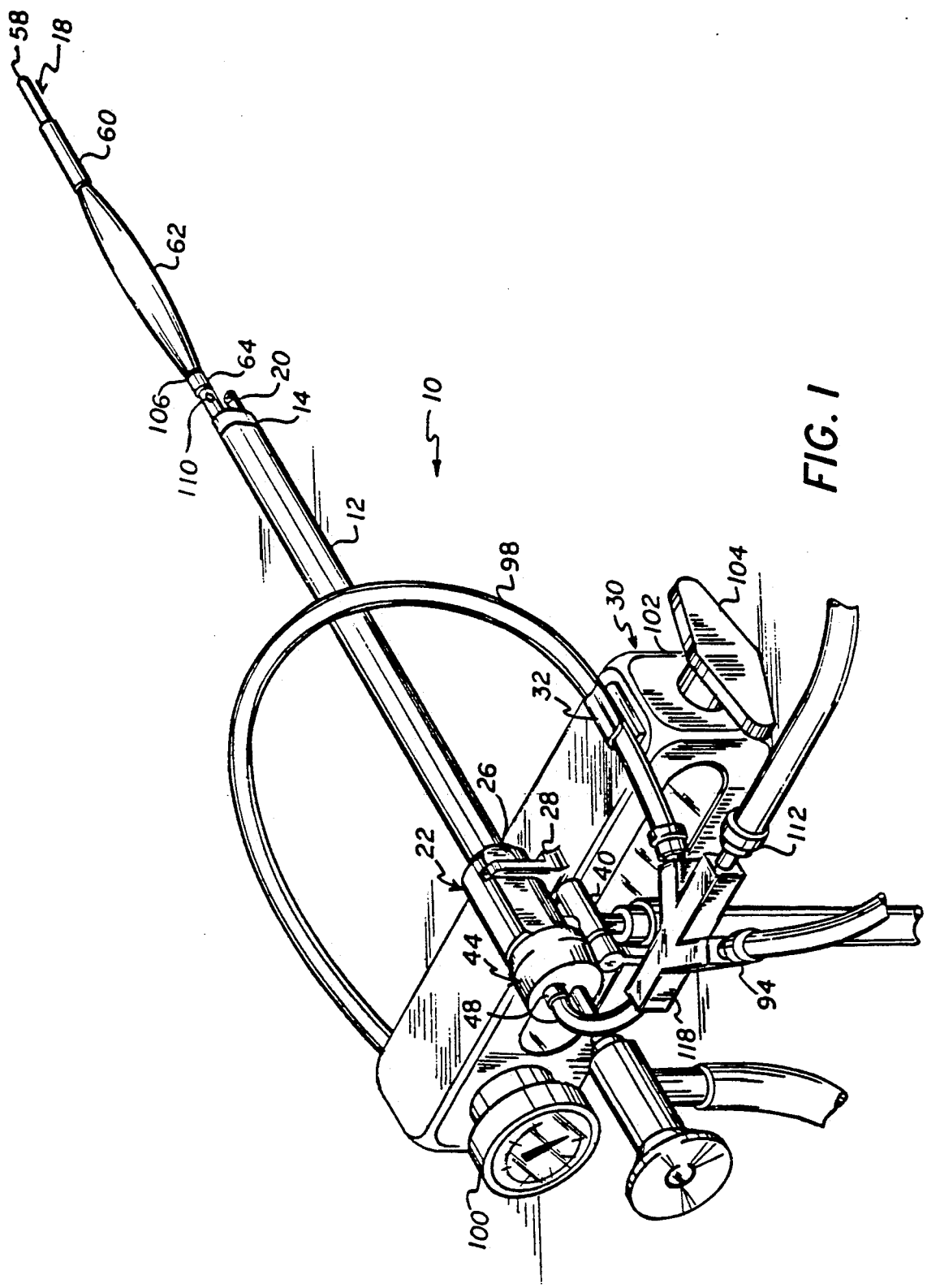
FIG. 1 is a perspective view of a dilatation catheter and sheath assembly in accordance with one embodiment of the present invention.
Figure 16:
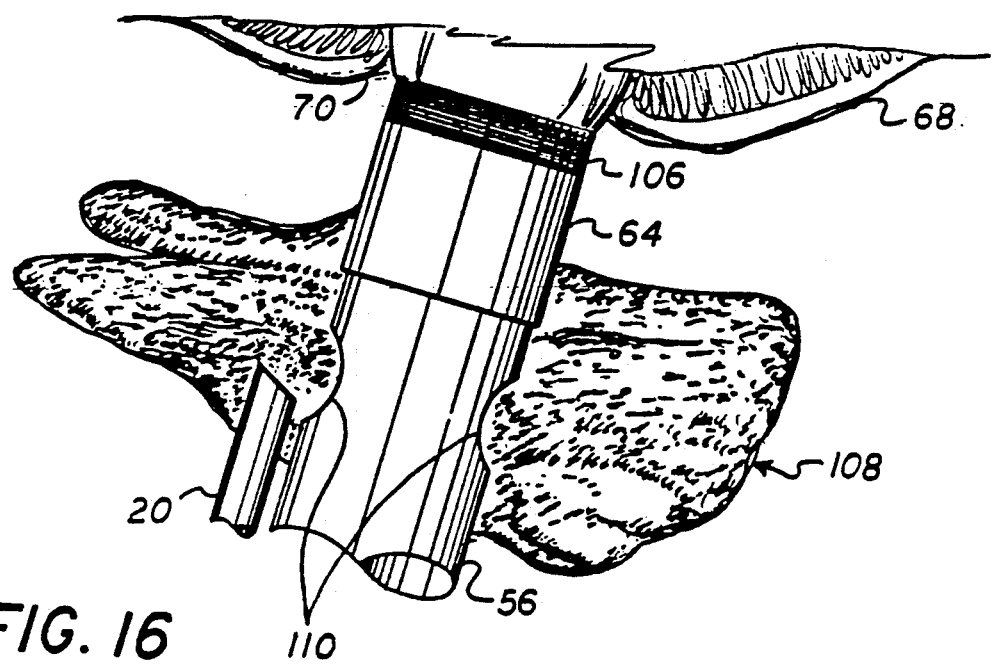
FIG. 16 is a magnified view of the marking disposed near the proximal end of the dilatation balloon showing clearance of the external sphincter muscle.

Referring now to the drawings in detail, wherein like reference numerals designate like elements throughout the several views thereof, there is shown generally at 10 in FIG. 1, a dilatation catheter and sheath assembly embodying the present invention in a preferred form. The sheath 12 is advantageously a substantially rigid, axially elongate hollow shaft throughout most of its length, but having a flexible distal tip 14. The sheath 12 exhibits an inner surface 16 which is substantially ellipsoid in cross-section, and is adapted to receive and guide an axially elongate catheter 18 and an endoscope 20 longitudinally therethrough. Advantageously, the particular endoscope used is known as a cystoscope.

In one embodiment of the invention, a cylindrical housing 22, disposed near the base of the sheath, exhibits a pair of grooves 24, formed upon two flattened surfaces 26 of the cylindrical housing 22, on opposite sides thereof. An end view of the cylindrical housing 22, as shown in FIG. 4, illustrates the ellipsoid shape of the inner walls 15 of the sheath 12, and the flattened side surfaces 26 thereof. A U-shaped clip 28 is integrally connected to the top of an inflation device 30 and is adapted to removably receive and retain the cylindrical housing 22 so as to enable the device 10 to be operated by one person, without the need for assistance. The removable attachment of the sheath 12 to the U-shaped clip 28 is illustrated in FIG. 2. A C-shaped clip 32 may also be provided on the body of the inflation device 30, to removably receive and retain the catheter therein and provide additional support for the proximal end of the device, thus controlling the catheter so it does not interfere with the eyepiece of the endoscope.

Situated on the underside 36 of the cylindrical housing 22 is a drainage port 38, having a cock valve 40 secured therein. The cock valve 40 is adapted to allow back-flowing fluids to escape the sheath 12 when positioned in the "on" position, and to prohibit the release of such fluids when in the "off" position.

The cylindrical housing 22 includes a hub portion 42, disposed at the proximal end thereof. A rubberized septum 44, preferably formed from a silicon rubber compound, is detachably placed onto the hub 42 of the cylindrical housing 22 so as to provide a seal therefor. As best seen in FIGS. 3 and 3a, the septum 44 is a circular cap 46, having a pair of boot sleeves 48, 50 integrally connected to the proximal end of the cap 46. In one embodiment, the septum 44 exhibits an outwardly extending boot sleeve 48 and inwardly extending boot sleeve 50. The boot sleeves 48, 50 are adapted to receive the cystoscope lens 20 and the dilatation catheter 18, and provide the septum 44 with elasticity at the point of contact therebetween. Without the presence of such sleeves, the rubberized septum 44 would itself deform if a force were applied to either the catheter 18 or cystoscope lens 20, thereby detracting from the septum's sealing ability. Further, the boot sleeves 48, 50 are adapted to readily adjust to and grip the outer diameter of the catheter 18 and lens 20 to yield a good seal therebetween. In an alternative embodiment, as shown in FIG. 3a, both of the boot sleeves 52, 54 extend outwardly from the septum cap 44. This embodiment is possible only when there exists sufficient room on the outside of the septum, such that a sharing of a common wall between the two sleeves is not necessitated.

As best seen in FIGS. 11, the dilatation catheter 18 of the present invention comprises an axially elongate catheter shaft 56, having a tapered guiding end 58, and a plurality of parallel conduits disposed therein. Situated near the guiding end 58 of the catheter shaft 56 is a locating balloon 60. The locating balloon 60 is a small latex Foley-type balloon, adapted for inflation by a source of pressurized fluid. Adjacent the locating balloon 60 is a larger dilatation balloon 62, having a proximal shoulder 64 and a distal shoulder 66.

A feature of this invention is that the distal shoulder 66 of the dilatation balloon 62 is overlapped by a portion of the locating balloon 60, such that, when the balloons are expanded, a minimal valley is left between the two balloons. Both of the balloons 60, 62 are bonded to the outer perimeter of the catheter shaft 56 by suitable adhesive or thermal process.

Figure 17:
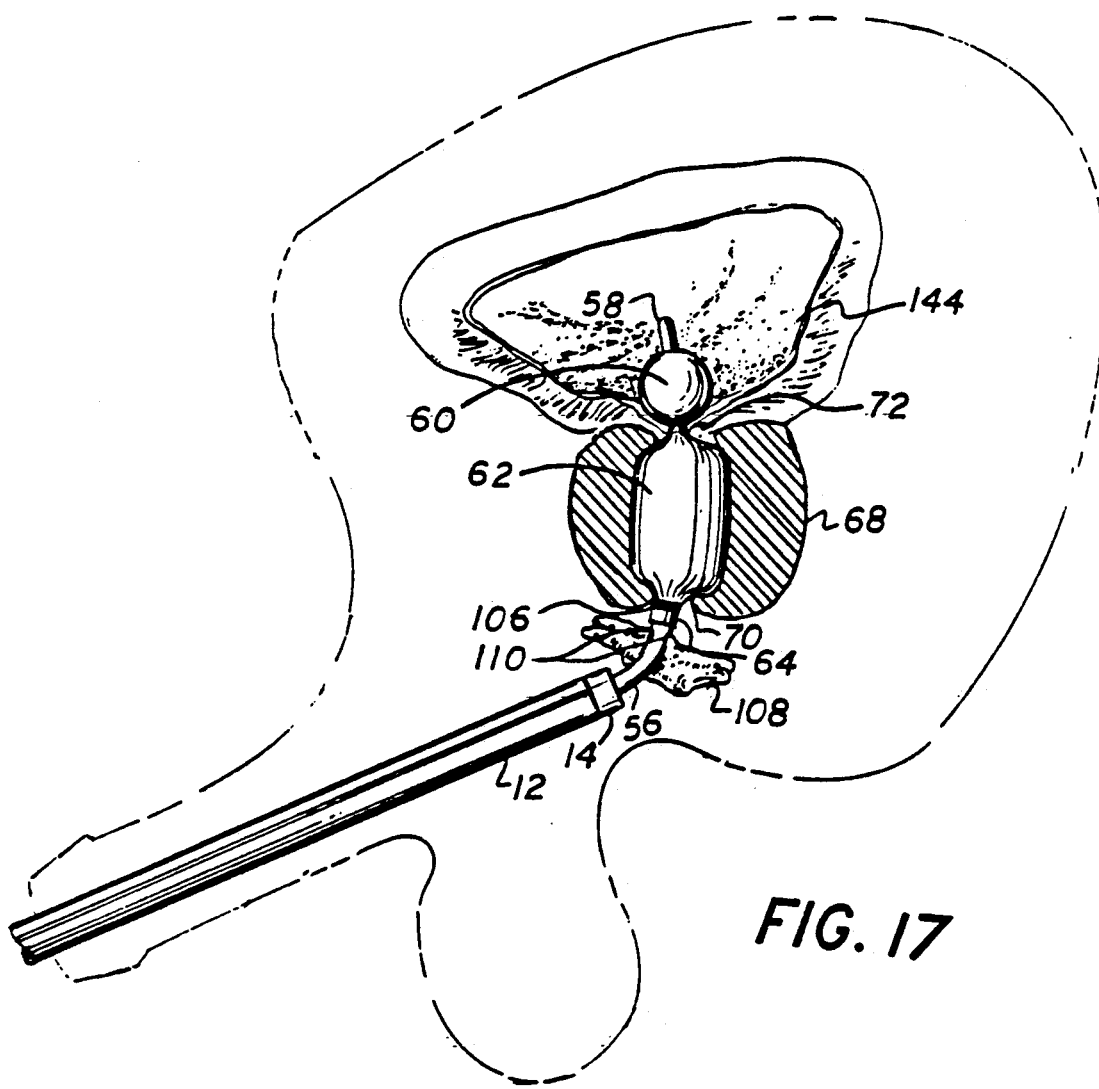
FIG. 17 is a cross-sectional view of the urethral dilatation catheter of the present invention operatively inserted within the male urinary tract.

While the overlap of the locating balloon 60 onto the shoulder 66 of the dilatation balloon 62 increases the area of dilatation by minimizing the distance between the locating balloon 60 and the dilatation balloon 62, suboptimal dilatation of the affected prostatic urethra 68 still exists due to the tapered nature of expandable balloons, commonly used in dilatation processes. To achieve optimal dilatation near the ends 70, 72 of the affected prostatic urethra 68, the dilatation balloon 62 can be molded with a steep, squared off end 74, as illustrated in FIG. 13. Depending on the nature of the affected area of the prostatic urethra 68, it may be desirable to enable urethral dilatation very close to the bladder neck 72 or the external sphincter muscle 70. Accordingly, either end of the dilatation balloon 62, neither end, or both ends may be provided with a substantially vertical configuration as illustrated in FIGS. 13, 14 and 17.

A material which is well adapted to construction of the dilatation balloon 62 of the present invention is polyethylene terephthalate (PET), such as KODAK's 9921. Preferably, the balloon 62 is extruded in a straight pipe configuration and then stretched and blown under high temperature and pressure to yield the desired shape 74. This type of technique is commonly applied in the making of angioplasty balloons. It should be noted that the PET material used to construct the dilatation balloon exhibits superior tensile strength characteristics to that of materials used in manufacturing other types of dilatation balloons, for example older angioplasty balloons. The PET material used to construct the dilatation balloon of the present invention has a tensile strength of between 20,000 to 50,000 psi, and is rated to withstand at least 3 atmospheres of pressure, and as much as 5 atm.

If a rubberized latex material were used to fabricate the dilatation balloon of the present invention, the walls of the balloon would necessarily be much thicker in order to withstand the exceedingly high pressures required for adequate dilatation of the affected prostatic urethra. Thus, the PET material, by virtue of its superior strength, allows a thinner balloon to be utilized. The thinness of the balloon thus formed, makes possible a dilatation balloon 62 which, in an uninflated state, conforms to the external walls of the catheter shaft 56, thereby providing a dilatation catheter 18 having substantially the same size and shape as the unstretched lumen. However, the increased strength of the material also dictates a balloon which is somewhat stiff and substantially less pliable than a latex balloon.

Consequently, when negative pressure is applied to collapse the dilatation balloon 62 made of the PET material, sharp ridges may form on the exterior surface thereof. Advantageously, the distal tip 14 of the introduction sheath 12 is formed of a flexible material, which readily deforms to the gross contours of the deflated dilatation balloon 62, so as to coerce the balloon 62 into the introduction sheath 12 prior to the withdrawal of the catheter 18 from the urethra. Preferably, the tip 14 is formed from a substantially malleable Poly Vinyl Chloride (PVC) compound, which is RF welded to rigid shaft portion 12 of the sheath.

To ensure that the catheter 18 is fully within the introduction sheath 12 prior to the withdrawal thereof, visual indicia, such as the marking 78 on the exterior shaft 56 of the catheter 18 is provided. As the catheter shaft 56 and deflated dilatation balloon 62 are gradually withdrawn from the urethra, the indicia 78 will be advanced out of the sheath 12. When the designated indicia 78 becomes visible, the catheter 18 is fully retracted within the sheath 12, and the device 10 may be withdrawn, without causing undue trauma to the urethral lumen.

As best seen in cross-section in FIG. 10, the catheter shaft 56 houses a pair of circular inflation conduits 80, 82 and an irrigation conduit 84. The inflation conduit 80 having an aperture 86 underlying the locating balloon 60 exhibits a tubular passageway which permits pressurized fluid to be transmitted into the chamber enclosed by the locating balloon 60, so as to selectively inflate the balloon 60 to a suitable level. Likewise, the inflation conduit 82 having a pair of inflation apertures 90, 92 underlying the dilatation balloon 62 allows pressurized fluid to selectively fill the balloon 62 to a desired level.

To facilitate inflation of the locating balloon 60, a simple fluid valve 94 may be connected to the proximal end of the conduit 80. This valve 94 is integrally connected to the inflation conduit 80 and may be easily manipulated to allow quick sealing of the conduit 80 and maintain the pressurized fluid within the balloon chamber 60 and the conduit 80. The locating balloon 60 may be pressurized by inserting a hypodermic syringe (not shown) into the valve 94, with the valve 94 in its open condition. By forcing fluid into the conduit 80, the locating balloon 60, at the distal end of the inflation conduit will be inflated. The valve 94 may then be closed, and the hypodermic syringe removed, leaving the locating balloon 60 in an inflated state.

Since inflation of the dilatation balloon 62 is more critical, the source of pressurized fluid 98 used to inflate the dilatation balloon 62 is connected to a pressure gauge 100. Preferably, the inflation device 98 includes a syringe barrel 102 having a threaded rod and ratchet mechanism 104 which replaces the conventional plunger. This configuration allows fine tuning of the pressure amassed within the dilatation balloon 62 by screw turning the threaded rod 104. It has been determined that an intra-balloon pressure of approximately 3 atm., or 45 p.s.i.g. is sufficient to force the prostate away from the urethral lumen to relieve the obstruction and reestablish normal micturition.

Proximate to the proximal end of the dilatation balloon 62, and encircling the proximal shoulder 64 thereof, is a heavy black line 106. Prior to inflating the dilatation balloon 62, care should be taken to ensure that the black line 106 does not extend onto any portion of the external urethral sphincter muscle 108. This is vitally important as accidental dilatation of the sphincter 108 may cause the patient to lose voluntary control over micturition, especially if the sphincter experiences plastic deformation, i.e., the inability to return to its original shape.

An important feature of this invention is the provision of an irrigation system. As described below, the system provides the dual features of both flushing blood away from the lens of the cystoscope to aid in the viewing of the external sphincter muscle and the black line 106 on the shoulder 64 of the dilatation balloon 62 and inhibiting coagulation of blood within the urethra. This flushing system includes a plurality of irrigation ports 110 disposed along the exterior shaft 56 of the catheter 18, proximate to the line 106 are provided. The irrigation ports 110 are adapted to continuously flush fluid, for example, saline, from the irrigation conduit 84, which extends through the center of the catheter shaft 56. The irrigation conduit 84 is provided with a coupling device 112 at the proximal end thereof, adapted to receive a source of flushing fluid, which, for example, can be a hanging container of saline (not shown), having a length of flexible tubing extending therefrom, for connection to the coupling device 112. The source of fluid is elevated and allowed to flow by gravity through the irrigation conduit 84 and out the irrigation ports 110, so as to flush blood away from the lens 20 and allow the urologist an unobstructed view of the external sphincter muscle 108 and the line 106 encircling the proximal shoulder 64 of the dilatation balloon 62.

In addition to permitting an unobstructed view of the proximal shoulder 64 of the balloon 62, the flushing of blood inhibits coagulation, and therefore substantially eliminates clotting within the urethral lumen. Backflowing flushing fluid and blood is drained from the urethra through introduction sheath 12 by gravity flow. A drainage reservoir (not shown) is connected to the cock valve 40 which, when in its open position, allows the back-flowing fluids to drain, by gravity flow, into the reservoir and subsequently disposed of. Alternatively, the flushing fluid can be supplied through the sheath 12 to flush blood away from the cystoscope lens 20. In this embodiment, the irrigation ports 110 of the irrigation conduit 84 function as influent ports to drain the flushing fluid and blood out of the urethra.

Located at the proximal end of the catheter shaft 56, and integrally connected thereto, is a Y-shaped plastic manifold 118. The manifold 118 is adapted to define and separate the trio of conduits 80, 82, 84 disposed within the body of the catheter shaft 56. Preferably, the manifold 118 is preformed in the Y-shaped configuration and is adapted to connect to the catheter shaft 56 and trio of conduits at the proximal end thereof. The catheter shaft 56 should be bent and cut to expose the inflation conduits 80, 82 respectively. The irrigation conduit 84 need not be exposed in this manner, as the manifold 118 includes a substantially straight portion in which the proximal end of the irrigation conduit 84 will reside. As shown in FIG. 9, during the molding process flexible core pins 122, 124 are inserted into the exposed inflation conduits 80, 82 to respectively maintain the openings into the inflation conduits and provide support therefor during the molding process. In a similar manner, a straight core pin 126 is inserted into the irrigation conduit 84, and the catheter 18 is set into the preformed plastic manifold 118. Plastic is then injected into the manifold 118 to form a tight seal, and the core pins 122, 124, 126 are removed after the plastic has hardened.

Method of Using the Dilatation Catheter

Prior to dilating the obstructed urethral lumen, the length of the affected prostatic urethra 68 should be measured. This may be accomplished by the use of a calibration catheter 128, as illustrated in FIG. 15. The calibration catheter 128 is an axially elongate shaft 130, having an expandable balloon 132 located near the distal end 134 thereof, and an inflation conduit (not shown) which extends substantially the entire length of the shaft 130. The expandable balloon 132 is adapted to be inflated through an inflation aperture 136, extending from the inflation conduit by a source of pressurized fluid (not shown). A plurality of graduated markings 138 extend along the exterior shaft 130 of the catheter 128, commencing near the proximal end 140 of the expandable balloon 132, and are adapted to be read from the distal end 134 of the catheter 128 to the proximal end 142.

The calibration catheter 128 is adapted to be received into the sheath of a standard cystoscope, and the cystoscope inserted into the urethra through the penile meatus. Once the distal end 134 and expandable balloon 132 of the calibration catheter 128 enters the bladder 144, the expandable balloon 132 may be inflated, and the catheter 128 slowly withdrawn from the urethra until the balloon 132 becomes lodged within the bladder neck 72. Graduated markings 138, inscribed on the exterior shaft 130 of the catheter 128 can be used to measure the distance between the bladder neck 72 and the lower end 70 of the affected prostatic urethra 68. Once such a measurement has been determined, the expandable balloon 138 may be deflated, and the catheter 128 withdrawn.

An introduction sheath 12, as illustrated in FIGS. 7 and 8 is then readied for insertion through the external urethral opening. An obturator 146, as shown in FIGS. 6, 7 and 8, having a smooth, tapered end 148 with no sharp edges is inserted into the sheath 12, and secured to the hub 42 of the cylindrical housing 22 by chamfered clips 150. The flexible tip 14 of the sheath 12 tapers inwardly, so as to grip the extending portion of the obturator 146 and provide a fairly smooth surface continuation of the introduction sheath. This mild transition between the obturator 146 and sheath 12 is instrumental in reducing damage and trauma to the tender urethral lumen. Once the sheath 12 has been fully inserted within the urethral lumen, the chamfered clips 150 may be released, and the obturator 146 withdrawn.

A catheter shaft 56, having a dilatation balloon 62 with a length approximately equivalent to that measured by the calibration catheter 128, is then inserted through one 48 of two boot sleeves of the septum 44, until at least that portion of the catheter shaft 56 to which the expansible balloons 60, 62 are attached extends therethrough. The septum 44 is then friction fit onto the hub 42 of the cylindrical housing 22 such that the catheter 18 is in alignment with the larger diameter ellipsoid section 152 of the sheath 12. The cystoscope lens 20 is then inserted into the other boot sleeve 50, and is then urged through the sheath 12 and into the urethra after placement of the catheter 18.

To provide support for the catheter 18, an elongate stylet 154 may be inserted into the irrigation conduit 84, as illustrated in FIG. 11. The stylet 154 facilitates the ease with which the catheter 18 may be inserted into the urethra, and may remain within the irrigation conduit 84 until the locating balloon 60 is disposed within the bladder 144, at which time the stylet 154 should be removed. Once the locating balloon 60 is within the bladder 144, the inflation conduit 80 may be coupled to a source of pressurized fluid so as to inflate the locating balloon 60. The catheter 18 is then gradually withdrawn from the bladder 144 until the balloon 60 is lodged within the bladder neck 72. When the locating balloon 60 is properly positioned within the neck 72 of the bladder 144, a seal is formed therebetween which prohibits fluids accumulating within the bladder 144 from travelling down the urethra and also prohibits fluids from flowing into and filling up the bladder from the urethra.

Once the catheter 18 has been properly situated with respect to the upper end 72 of the affected prostatic urethra 68, the irrigation conduit 84 may be connected to a source of flushing fluid. The flushing fluid is gravity fed through the irrigation conduit 84 and out the irrigation ports 110, so as to wash existent blood away from the cystoscope lens 20 and provide the urologist with an unobstructed view of the proximal shoulder 64 of the dilatation balloon 62, and adjacent organs. Looking through the cystoscope, the urologist can manipulate the catheter 18 to confirm that the dilatation balloon 62 is clear of the external urethral sphincter muscle 108, so as to ensure that the sphincter 108 will not inadvertently be dilated.

Upon properly positioning the dilatation balloon 62 with respect to both the bladder neck 72 and the sphincter 108, the inflation conduit 82 for the dilation balloon 62 may be connected to a source of pressurized fluid 98. As described above, the inflation source 98 should enable a accurate, progressive dilation under constant control of the pressure being applied within the dilatation balloon 62. The device remains within the affected prostatic urethra 68, until sufficient pressure dilatation has been achieved. Subsequent to attaining adequate pressure dilation of the prostatic urethra, and eliminating the urinary outflow obstruction, the balloons 60, 62 may be deflated, releasing the pressurized fluid therefrom.

As the dilatation balloon 62 is deflated, sharp ridges may form on the outer surface thereof, due to the stiffness of the material from which it was formed. As shown in FIG. 5, the flexible tip 14 of the introduction sheath 12 readily deforms and flares, so as to coerce the dilatation balloon 62 back into the sheath 12. When the marking 78, indicative of the time at which the dilatation balloon 62 is completely within the sheath 12 becomes visible, the device may be withdrawn from the urethra.

In view of the medical treatment to be administered in using the device of the present invention, it is necessary that the device be aseptically clean. Accordingly, the dilatation catheter and sheath can be cleansed and sterilized readily and easily either prior to use thereof, or packaged in this condition, available for immediate use. Further, both the catheter and sheath may be discarded after use, negating the need for recleaning and resterilization.

It will be appreciated that certain structural variations may suggest themselves to those skilled in the art. The foregoing detailed description is to be clearly understood as given by way of illustration, the spirit and scope of this invention being limited solely by the appended claims.

What is claimed is:

1. An intraurethral dilatation apparatus for relieving the symptoms of obstructive prostatism, said device comprising:
   an axially elongate introduction sheath, adapted for insertion into the urethra to receive and guide both a catheter shaft and a cystoscopic lens therethrough, so as to minimize trauma to the urethral lining during the insertion of said catheter and said lens;
   a tubular, axially elongate, catheter shaft for insertion through said sheath, having a distal end to facilitate manipulation of said device within the urethra;
   an expansible locating balloon, disposed near the distal tip of said catheter shaft and bonded thereto; and
   a dilatation balloon, on said catheter shaft situated proximally of said expansible locating balloon, said dilatation balloon outwardly radially expandable to a preselected configuration in response to inflation thereof, wherein said dilatation balloon exhibits proximal and distal shoulders, and wherein a portion of said locating balloon overlaps at least a portion of said distal shoulder of said dilatation balloon.

2. An intraurethral dilatation apparatus for relieving the symptoms of obstructive prostatism, said device comprising:

an axially elongate introduction sheath, adapted for insertion into the urethra to receive and guide both a catheter shaft and a cystoscopic lens therethrough, so as to minimize trauma to the urethral lining during the insertion of said catheter and said lens;

a tubular, axially elongate, catheter shaft for insertion through said sheath, having a distal end to facilitate manipulation of said device within the urethra;

an expansible locating balloon, disposed near the distal tip of said catheter shaft and bonded thereto; and a dilatation balloon, on said catheter shaft situated proximally of said expansible locating balloon, said dilatation balloon outwardly radially expandable to a preselected configuration in response to inflation thereof, wherein said dilatation balloon is made of a less resilient material than said locating balloon, and wherein said dilatation balloon, after being deflated, remains in a somewhat enlarged state, and wherein said introduction sheath has flexible tip at the distal end thereof adapted to temporarily deform upon receiving said enlarged dilatation balloon, so as to coerce said balloon back to said sheath prior to the removal of said device.

3. A method of treating the symptoms of obstructive prostatism, comprising the steps of:

measuring the length of the affected prostatic urethra using a calibration catheter;

inserting an introduction sheath into the urethra through the penile meatus using an obturator;

inserting a dilatation catheter, having a location balloon and a dilatation balloon secured thereto, and a standard endoscopic lens into said introduction sheath;

inflating said locating balloon and gradually withdrawing said catheter from the urethra, so as to lodge said locating balloon in the neck of the bladder;

visually confirming proper positioning of said dilatation balloon with respect to the external urethral sphincter; and inflating said dilatation balloon so as to radially outwardly dilate said obstruction.

4. A method as defined by claim 3, further comprising:

providing an irrigation system within said catheter, said irrigation system adapted to flush blood away from said endoscopic lens, so as to facilitate enhanced visualization within the urethra.

5. In an intraluminal introduction sheath of the type for insertion into a body lumen for facilitating in vivo removal of a catheter having a compressible portion which is somewhat larger in cross-section than the inner cross-section of said sheath, said sheath having an axially elongate hollow shaft providing a path through which said catheter is guided into and out of a body lumen; the improvement comprising:

a tip attached to the intraluminal end of said shaft, said tip formed of a material substantially more flexible than that of said shaft so that said tip will temporarily deform in response to the contours of said compressible portion of said catheter so as to facilitate compression and withdrawal of said compressible portion of said catheter.

6. A method of treating the symptoms of obstructive prostatism by dilatation of the prostatic urethra, comprising the steps of:

inserting a dilatation means into the urethra, said dilatation means having an associated visualization means within the urethra for positioning the dilatation means relative to an anatomical landmark within the urethra;

adjusting the location of the dilatation means within the urethra with respect to the anatomical landmark using said visualization means; and expanding said dilatation means so as to radially outwardly dilate said obstruction.

7. A method of treating the symptoms of obstructive prostatism as in claim 6, wherein said adjusting step comprises visually observing the location of an anatomical landmark using an endoscope.

8. A method as in claim 6 wherein the visualization means comprises a visual transmission means introduced substantially in parallel to the catheter within at least a portion of the urethra.

9. A method of treating the symptoms of obstructive prostatism as in claim 6, further comprising a step of flushing the visual field of the visualization means with a substantially visually transparent flushing fluid to optimize vision through the visualization means.

10. A method of treating the symptoms of obstructive prostatism by dilatation of the prostatic urethra, comprising the steps of:

inserting a dilatation means into the urethra, said dilatation means having an associated non-radiological locating means for positioning the dilatation means relative to an anatomical landmark within the urethra, said locating means being proximal to said dilatation means;

locating the position of the dilatation means within the urethra using said non-radiological locating means;

adjusting the location of the dilatation means within the urethra with respect to the anatomical landmark using said non-radiological locating means; and expanding said dilatation means so as to radially outwardly dilate said obstruction.

11. A method of treating the symptoms of obstructive prostatism as in claim 10, wherein said non-radiological locating means in the adjusting step permits direct vision of the anatomical landmark.

12. A method of treating the symptoms of obstructive prostatism as in claim 11, wherein said direct vision locating means is an endoscopic viewing system.

13. A method of treating the symptoms of obstructive prostatism as in claim 10, wherein the dilatation means is disposed on a triple lumen catheter.

14. An intraurethral dilatation apparatus for relieving the symptoms of obstructive prostatism, said device comprising:

an axially elongate introduction sheath, adapted for insertion into the urethra to receive and guide both a catheter shaft and a cystoscopic lens therethrough, so as to minimize trauma to the urethral lining during the insertion of said catheter and said lens;

a tubular, axially elongate, catheter shaft for insertion through said sheath, having a distal end to facilitate manipulation of said device within the urethra;

a locating balloon, disposed on said catheter shaft and bonded thereto; and a dilatation balloon, on said catheter shaft situated adjacent to said locating balloon, said dilatation balloon outwardly radially expandable to a preselected configuration in response to inflation thereof, wherein said dilatation balloon is made of a less resilient material than said locating balloon, and wherein said dilatation balloon, after being deflated, remains in a somewhat enlarged state, and wherein said introductions heat has a flexible tip at the distal end thereof adapted to temporarily deform upon receiving said enlarged dilatation balloon, so as to coerce said balloon back into said sheath prior to the removal of said device.

15. A method for providing substantially continuous visual verification of the position of an intraurethral dilatation balloon catheter apparatus even when existent blood and other fluids caused by the medical procedure are blocked by said dilatation balloon from flowing into the patient's bladder, comprising the steps of:

inserting into the urethra a dilatation catheter shaft having a dilatation balloon secured thereto;

viewing the location of said apparatus within the urethra to position said dilatation balloon within said urethra;

inflating said dilatation balloon to substantially obstruct the urethra so that passage of said existent blood and fluids from the proximal side of said balloon to the bladder is blocked;

flowing an irrigation flushing fluid substantially parallel to said shaft from outside the patient to said viewing location; and draining said flushing fluid along with said existent blood and fluids substantially parallel to said shaft away from said viewing location.

16. A method of treating the symptoms of obstructive prostatism, comprising the steps of:

inserting into the urethra a dilatation catheter shaft having a dilatation balloon secured thereto, a visual marking on the exterior wall of said catheter shaft, an irrigation conduit substantially parallel to said catheter shaft, and an irrigation port at the distal end of said irrigation conduit associated with said catheter shaft;

inserting a cystoscopic lens into the urethra after initial placement therein of the uninflated dilatation balloon;

flowing a flushing fluid through said irrigation port to wash away existent blood from said cystoscopic lens and draining said flushing fluid and blood from the region of said cystoscopic lens;

positioning said catheter shaft by viewing the position of said visual marking relative to the external urethral sphincter muscle so as to avoid accidental dilatation of the sphincter;

flowing pressurized fluid into said dilatation balloon for dilating said balloon until sufficient pressure dilatation is achieved to dilate the urethra and prostate thereby treating the urinary outflow obstruction;

withdrawing said fluid from said dilatation balloon so that said balloon is deflated; and withdrawing said cystoscopic lens and said dilatation catheter from the urethra.

* * * * *